United States Patent [19]

Rice

[11] Patent Number: 5,603,920
[45] Date of Patent: Feb. 18, 1997

[54] DENTIFRICE COMPOSITIONS

[75] Inventor: David E. Rice, Cincinnati, Ohio

[73] Assignee: The Proctor & Gamble Company, Mason, Ohio

[21] Appl. No.: 312,353

[22] Filed: Sep. 26, 1994

[51] Int. Cl.$^6$ .................... A61K 7/16; A61K 7/18
[52] U.S. Cl. ............... 424/49; 51/308; 423/335; 423/339; 414/52
[58] Field of Search ......................... 424/49–58

[56] References Cited

U.S. PATENT DOCUMENTS

| | | | |
|---|---|---|---|
| 3,003,919 | 10/1961 | Broge | 424/49 |
| 3,151,027 | 9/1964 | Cooley et al. | 167/93 |
| 3,325,368 | 6/1967 | Wood | 167/93 |
| 3,450,813 | 6/1969 | Muhler | 424/52 |
| 3,574,823 | 4/1971 | Roberts et al. | 424/49 |
| 3,955,942 | 5/1976 | Cordon et al. | 51/295 |
| 3,988,162 | 10/1976 | Wason | 106/288 |
| 3,989,814 | 11/1976 | Cordon et al. | 424/57 |
| 4,040,858 | 8/1977 | Wason | 106/288 B |
| 4,060,599 | 11/1977 | Cordon | 424/49 |
| 4,067,746 | 1/1978 | Wason et al. | 106/288 B |
| 4,075,316 | 2/1978 | Cordon | 424/49 |
| 4,089,943 | 5/1978 | Roberts et al. | 424/49 |
| 4,122,160 | 10/1978 | Wason | 424/49 |
| 4,141,969 | 2/1979 | Mitchell | 424/52 |
| 4,170,634 | 10/1979 | Cordon et al. | 424/49 |
| 4,174,387 | 11/1979 | Cordon et al. | 424/52 |
| 4,187,288 | 2/1980 | Cordon et al. | 424/49 |
| 4,272,509 | 6/1981 | Wason | 424/49 |
| 4,340,583 | 7/1982 | Wason | 424/52 |
| 4,376,762 | 3/1983 | Hauschild et al. | 424/49 |
| 4,376,763 | 3/1983 | Barth et al. | 424/49 |
| 4,412,983 | 11/1983 | Mitchell | 424/52 |
| 4,420,312 | 12/1983 | Wason | 51/308 |
| 4,421,527 | 12/1983 | Wason | 51/308 |
| 4,632,826 | 12/1986 | Plöger et al. | 424/52 |
| 4,664,907 | 5/1987 | Müller | 424/52 |
| 4,704,270 | 11/1987 | Müller et al. | 424/49 |
| 4,705,679 | 11/1987 | Müller et al. | 424/52 |
| 4,988,369 | 1/1991 | Akay | 51/293 |
| 5,110,574 | 5/1992 | Reinhardt et al. | 423/335 |
| 5,225,177 | 7/1993 | Wason et al. | 423/339 |
| 5,279,815 | 1/1994 | Wason et al. | 424/52 |
| 5,320,830 | 6/1994 | Lukacovic et al. | 424/52 |
| 5,320,831 | 6/1994 | Majeti et al. | 424/52 |
| 5,389,360 | 2/1995 | Mobley et al. | 424/49 |
| 5,431,903 | 7/1995 | Majeti et al. | 424/52 |
| 5,437,856 | 8/1995 | Lukacovic et al. | 424/50 |

FOREIGN PATENT DOCUMENTS

| | | | |
|---|---|---|---|
| 0535943 | 4/1993 | European Pat. Off. | A61K 7/16 |
| WO92/02454 | 2/1992 | WIPO | A61K 7/16 |

*Primary Examiner*—Shep K. Rose
*Attorney, Agent, or Firm*—David K. Dabbiere; Douglas C. Mohl; Jacobus C. Rasser

[57] ABSTRACT

Oral compositions, such as oral gels and toothpastes, containing a novel abrasive.

18 Claims, No Drawings

DENTIFRICE COMPOSITIONS

TECHNICAL FIELD

The present invention relates to dentifrice compositions such as toothpastes, which provide improved oral cleaning.

BACKGROUND OF THE INVENTION

A satisfactory dentifrice composition should have a cosmetic effect upon the teeth, namely, keeping them light colored. It should also clean and remove debris as well, thereby aiding the prevention of tooth decay and promoting gingival health. Abrasives aid in the removal of the tightly adherent pellicle film. This film usually comprises a thin acellular, glycoprotein-mucoprotein coating which adheres to the enamel within minutes after teeth are cleaned. The presence of various food pigments lodged within the film accounts for most instances of teeth discoloration. Ideally, an abrasive should provide satisfactory removal (cleaning) of the pellicle film with minimal damage (abrasion) to oral tissue, i.e. the dentin and enamel.

Beyond the pellicle cleaning aspect, incorporating an antiplaque agent(s) provides additional benefits. The formation of dental plaque is the primary source of dental caries, gingival and periodontal disease, and tooth loss. Plaque is a mixed matrix of bacteria, epithelial cells, leukocytes, macrophages and other oral exudate The bacteria associated with plaque can secrete enzymes and endotoxins which can irritate the gums and cause an inflammatory gingivitis. As the gums become increasingly irritated by this process, they have a tendency to bleed, lose their toughness and resiliency, and separate from the teeth. This separation results in periodontal pockets leading in turn to further accumulation of debris, secretions, and more bacteria/toxins. This process eventually leads to destruction of both the hard and soft tissue of the oral cavity.

The use of a variety of agents to clean the oral cavity and reduce plaque and mouth malodor has been recognized for some time. Examples include: U.S. Pat. No. 3,696,191, Oct. 3, 1972 to Weeks; U.S. Pat. No. 3,991,177, Nov. 9, 1976 to Vidra et al.; U.S. Pat. No. 4,058,595, Nov. 15, 1977 to Colodney; U.S. Pat. No. 4,115,546, to Vidra et al.; U.S. Pat. No. 4,138,476, Feb. 6, 1979 to Simonson et al.; U.S. Pat. No. 4,140,758, Feb. 20, 1979 to Vidra et al.; U.S. Pat. No. 4,154,815, May 15, 1979 to Pader; U.S. Pat. No. 4,737,359, Apr. 12, 1988 to Eigen et al.; U.S. Pat. No. 4,986,981, Jan. 22, 1991 to Glace et al.; U.S. Pat. No. 4,992,420, Feb. 12, 1991 to Nesser; U.S. Pat. No. 5,000,939, Mar. 19, 1991 to Dring et al.; Kokai 02/105,898, published Apr. 18, 1990 to Kao Corporation; Kokai 03/128,313, published May 31, 1991 to Nippon Kotai Kenkyu and Kokai 03/223,209, published Oct. 2, 1991 to Lion Corporation; U.S. Pat. No. 4,652,444, Mar. 24, 1987 to Maurer; U.S. Pat. No. 4,725,428, Feb. 16, 1988 to Miyahara et al.; U.S. Pat. No. 4,355,022, Oct. 19, 1982 to Rabussay and PCT application WO 86/02831, published May 22, 1986 to Zetachron, Inc.

Abrasives are described in U.S. Pat. No. 4,340,583, Jul. 20, 1982 to Wason, U.S. Pat. No. 3,574,823, Apr. 13, 1971 to Roberts et al., EP Patent 535,943A1, Apr. 7, 1993, McKeown et al., and PCT Patent WO 92/02454, Feb. 20, 1992 to McKeown et al.

In spite of the many disclosures relating to compositions for pellicle cleaning and antiplaque activity, the need for improved products still exists. The present inventor has developed oral compositions providing improved pellicle cleaning. Specifically, the present inventor has developed oral compositions incorporating a novel silica abrasive and an improved plaque reducing system.

It is therefore an object of the present invention to provide an oral care product and methods of using the same directed at pellicle cleaning. It is a further object of the present invention to provide compositions and methods which are effective in arresting the accumulation of plaque and preventing gum disease. A still further object of the present invention is to provide compositions that will also abate subsequent calculus formation.

These objectives and additional objectives will become readily apparent from the detailed description which follows.

SUMMARY OF THE INVENTION

The present invention relates to dentifrice compositions comprising:

a. a precipitated silica, said precipitated silica being a low structure precipitated silica having a narrow particle size range distribution of soft particles and having a mean value (MV) particle size ranging from 8 to 14 microns, an oil absorption ranging from 60 to 120 cc/100 g, and a mercury intrusion (HGI) void volume of 1.0 to 4.0 cc/g; said precipitated silica, when formulated into a dentifrice, having a Pellicle Cleaning Ratio (PCR) of from 70 to 140 and a Radioactive Dentin Abrasion (RDA) value of from 60 to 130; and wherein the ratio of said PCR to said RDA is at least 1.1; and wherein, as the particle size in microns increases in said silica, the RDA value remains substantially constant; and b. from about 0.1% to about 99% of an orally-acceptable dentifrice carrier.

The present invention further relates to a method of cleaning teeth reducing plaque, gingivitis and calculus using the above compositions.

All percentages and ratios herein are by weight unless otherwise specified. PCR and RDA are unitless. Additionally, all measurements are made at 25° C. unless otherwise specified.

DETAILED DESCRIPTION OF THE INVENTION

By "safe and effective amount," as used herein, means a sufficient amount to reduce stain and/or plaque/gingivitis without harming the tissues and structures of the oral cavity.

By the term "orally-acceptable carrier," as used herein, means a suitable vehicle which can be used to apply the present compositions to the oral cavity in a safe and effective manner.

The pH of the present herein described compositions range from about 6.5 to about 9.5, with the preferred pH being from about 6.5 to about 9.0 and the most preferred pH being 7.0 to about 9.0.

The essential as well as optional components of the compositions of the present invention are described in the following paragraphs.

Abrasive

The precipitated silicas of the present invention provide unique Radioactive Dentin Abrasion (RE)A) values in the dentifrice compositions of the present invention and are characterized by having a mean value particle size (MV) as measured on a Microtrac Particle Analyzer, in the range of 8 to 14 microns and more preferably from 8–10 microns. The mean value (MV) particle size takes into account skewed particle sizes and speaks to distribution of the particle. Thus, as the mean particle size increases over the range of 8–14 microns as disclosed herein, it would be expected that the RDA would also increase. However, the RDA of these silicas is relatively lower and remains relatively constant or increases at a slower rate. These silicas also have good fluoride compatibility.

Certain of these precipitated silicas can also be characterized as agglomerated or cohered silicas wherein subparticles are cohesively bound together during the process of acidulation and/or curing to form the agglomerated precipitated silicas having the mean particle size of 8 to 14 microns. Preferably greater than about 2%, more preferably greater than about 5%, even more preferably greater than about 10% and most preferably greater than about 15% by weight of the precipitated silica particles of the present invention are made up of these agglomerates. Agglomeration is not a result of the addition of a binding agent to the process, but rather is a natural agglomeration caused by physical binding characteristics of the subparticles. It is theorized that during digestion and subsequent curing, the particles of silica become more uniform in size by a process of cohesion of smaller particles and breaking apart of large agglomerates.

It is therefore theorized that when used in dentifrice formulations, the agglomerated particles break down during the brushing process when in contact with dentin or enamel so that the precipitated silica particles appear to be sorer particles when used in the dentifrice formulations. This property, when considered with the fact that the precipitated silicas already possess lower RDA values than prior art silicas, provides dentifrice compositions with increased cleaning but lower abrasiveness. Therefore, a feature of the precipitated silicas of the invention is that they are agglomerated precipitated amorphous silicas of substantially uniform particle size and having mean particles sizes of 8 to 14 microns, and more preferably from 8 to 10 microns, and which have reduced RDA values as compared to the prior art.

A feature of these precipitated silicas is the relationship of the mean particle size and exhibited RDA. The precipitated silicas of the invention have a mean particle size of 8–14 microns and also unexpectedly have a relatively lower abrasivity or hardness. This relatively lower abrasivity for a low structure silica is unique to the precipitated silicas of the invention.

The precipitated silicas of the invention are Low Structure silicas in accordance with the definitions set forth in the J. Soc. Cosmet. Chem. 29., 497–521 (August, 1978), and Pigment Handbook: Volume 1, Properties and Economics, Second Edition, Edited by Peter A. Lewis, John Wiley & Sons, Inc., 1988, p. 139–159. Further, the precipitated silicas may be characterized as having an oil absorption ranging from 60 to 120 cc/100 g and preferably 80 to 100 cc/100 g, more preferably about 90 cc/100 g. The silicas may also be characterized as having a BET surface area in the range of 50 to 250 $m^2/g$.

A further feature of the precipitated amorphous silicas of the invention is the porosity as determined by mercury intrusion (HGI) void volume measurements. The silicas of this invention have mercury intrusion values in the range of 1.0 to 4.0 cc/g and preferably 1.5 to 2.5 cc/g. A further feature of the precipitated silicas of the invention resides in the pH which ranges from 4.0 to 8.5 and preferably from 6.5 to 8.5, as measured in a 5% aqueous slurry.

The Pellicle Cleaning Ratio (PCR) of the inventive silica, which is a measurement of the cleaning characteristics of a dentifrice, ranges from 70 to 140 and preferably from 100 to 130 for the precipitated silica of the invention. The Radioactive Dentin Abrasion (RDA) of the inventive silicas, which is a measurement of the abrasiveness of the precipitated silicas of the invention when incorporated into a dentifrice, ranges from 60 to 130, preferably from 60 to 100, and more preferably from 80 to 90.

The silicas of the invention may also be characterized as having a pour density ranging from 12–16 $lb./ft^3$, a pack density ranging from 25–30 $lb./ft^3$ and median average particle size ranging from 7.0 to 11.0.

These silicas, when incorporated into a dentifrice composition provide an improved PCR/RDA ratio. The PCR/RDA ratio is used to determine the relative ratio of cleaning and abrasion characteristics of a dentifrice formulation. Commercially available dentifrice formulations generally have a PCR/RDA ratio in the range of 0.5 to below 1.0. The precipitated silicas used in the compositions of the present invention provide PCR to RDA ratios to dentifrice formulations of greater than 1, usually in the range of 1.1 to 1.9, but more preferably in the range 1.2 to 1.9.

The precipitated silicas of the invention are preferably characterized as synthetic hydrated amorphous silicas, also known as silicon dioxides or $SiO_2$. This definition is intended to include gels and hybrids of silicas such as Geltates.

Although not bound by theory, it is believed that this invention results in relatively softer silica abrasives than would be predicted by the prior art.

The RDA (Radioactive Dentin Abrasion) values are determined according to the method set forth by Hefferren, Journal of Dental Research, July–August 1976, pp. 563–573, and described in the Wason U.S. Pat. Nos. 4,340,583, 4,420,312 and 4,421,527, which publication and patents are incorporated herein by reference.

The PCR (Pellicle Cleaning Ratio) cleaning values are determined by a slightly modified version of the PCR test described in "In Vitro Removal of Stain With Dentifrice", G. K. Stookey, T. A. Burkhard and B. R. Schemerhorn, J. Dental Research, 61, 1236–9, 1982. Cleaning is assessed in vitro by use of the modified pellicle cleaning ratio test. This test is identical to that described by Stookey et al. with the following modifications: (1) a clear artificial pellicle film is applied to bovine chips prior to application of the stained film, (2) solution heating is used rather than radiative heating during film application, (3) the number of brush strokes is reduced to 200 strokes and (4) the slurry concentration is 1 part dentifrice to 3 parts water.

In the present specification, oil absorption is measured using the ASTM rubout method D281. Surface area is determined by the BET nitrogen adsorption method of Brunaur et al., J. Am. Chem. Soc., 60, 309 (1938). To measure brightness, fine powder materials that are pressed into a smooth surfaced pellet are evaluated using a Technidyne Brightimeter S-5/BC. This instrument has a dual beam optical system where the sample is illuminated at a angle of 45°, and the reflected light viewed at 0°. It conforms to TAPPI test methods T452 and T646, and ASTM Standard D985. A series of filters direct to reflected light of desired wavelengths to a photocell where it is converted to an output voltage. This signal is amplified and then processed by an internal microcomputer for display and printout.

The average particle size (mean value and median or 50%) is measured using a Microtrac II apparatus, Leeds and Northnap. Specifically, a laser beam is projected through a transparent cell which contains a stream of moving particles suspended in a liquid. Lights rays which strike the particles are scattered through angles which are inversely proportional to their sizes. The photodetector array measures the quantity of light at several predetermined angles. Electrical signals proportional to the measured light flux values are then processed by a microcomputer system to form a multichannel histogram of the particle size distribution.

The pore volumes (mercury pore volume) are determined using an Autopore II 9220 Porosimeter (Micromeritics Corporation). This instrument measures the void volume and pore size distribution of various materials. Mercury is forced into the voids as a function of pressure and the volume of mercury intruded per gram of sample is calculated at each pressure setting. Total pore volume expressed herein represents the cumulative volume of mercury intruded at pressures from vacuum to 60,000 psi. Increments in volume (cc/g) at each pressure setting are plotted against the pore radius corresponding to the pressure setting increments. The peak in the intruded volume versus pore radius curve corresponds to the mode in the pore size distribution. It identifies the most common pore size in the sample.

Bulk density is measured by measuring the volume in liters occupied by a given weight of the abrasive and is reported in pounds per cubic foot.

The silicas can be further characterized using a Einlehner At-1000 Abrader to measure the softness of the silicas in the following manner: A Fourdrinier wire screen is weighed and exposed to the action of a 10% aqueous silica suspension for a certain length of time. The amount of abrasion is then determined as milligrams weight lost of the Fourdrinier wire screen per 100,000 revolutions. Brass Einlehner (BE) results are expressed in milligrams.

The silicas preferably possess a BE of less than about 7 and preferably between 2 and 5.

These precipitated silicas are prepared by a fresh water acidulation process wherein silica (silicon dioxide or $SiO_2$) is precipitated by reaction of an alkali metal silicate and a mineral acid in aqueous solution. The alkali metal silicate may be any alkali metal silicate, but sodium silicate is preferred. While any mineral acid may be used in the process, sulfuric acid is a preferred reactant.

It is a feature of the invention that the process of preparation is a fresh water process, that is, no electrolyte such as alum, $Na_2SO_4$, or NaCl, is present during the reaction.

In the preferred process, an aqueous sodium silicate solution is provided wherein the sodium silicate is present in a concentration of about 8.0 to 35 weight percent, preferably 8.0 to 15 weight percent. The $Na_2O:SiO_2$ ratio in the silicate solution should range from about 1 to 3.5:1 and preferably from 2.5 to 3.4:1. The sulfuric acid reactant will preferably have a concentration of about 6 to 35% in water, preferably about 9.0 to 15 weight percent.

In the preferred procedure, a small portion of the sodium silicate solution is charged to a reactor for reaction with the sulfuric acid and the remainder of the silicate. In the preferred embodiment, only about 1 to 5% of the total stoichiometric amount of sodium silicate solution, preferably about 2%, should be initially placed in the reactor to serve as initiating nuclei for the silica. This aqueous solution of sodium silicate is then preheated to a temperature in the range of about 80° to 90° C. with agitation prior to the addition of the sulfuric acid and remainder of sodium silicate. Agitation may be provided by conventional stirring of agitation equipment. Thereafter with continued agitation, the remainder of the sodium silicate and sulfuric acid are separately slowly added to the reactor over a limited period of time. In the preferred embodiment, the sodium silicate is metered into the reaction mixture at the rate of about 7 to 12 liters per minute and, more preferably, at the specific rate of 8.94 liters per minute. The sulfuric acid is metered into the reactor at the rate of about 1 to 4 liters per minute but more preferably at the rate of about 2.95 liters per minute.

The sodium silicate solution and sulfuric acid are metered into the sodium silicate solution in the reactor over an addition time of about 40 to 60 minutes, but preferably over a 50 minute addition time. At the end of this addition time at which point the silica has precipitated, the sodium silicate solution addition is stopped but sulfuric acid addition is continued with agitation until a final pH of 5.0 to 5.8 is obtained in the reactor. At this stage, the silica has precipitated to provide a mixture of the precipitated silica and the reaction liquor.

After precipitation of the silica and lowering of the pH of the mixture, the reaction mixture is then subjected to digestion and curing. Digestion is carried out by raising the temperature of the mixture to a temperature of 90° to 98° C., preferably about 95° to 98° C., with continued agitation, over a residence time of about 5 minutes to an hour preferably about 10 to 30 minutes.

Thereafter, the product is cured by further raising the temperature of the mixture to a temperature in the range of about 100° C. with continued agitation so as to boil the reaction mixture over a cure time of about one-half hour to about two hours, preferably about 30 minutes to 80 minutes, more preferably about 1 hour. Digestion and curing procedures are critical features of the invention.

On completion of the reaction, the pH is again adjusted to about 5.0, and reaction mixture is filtered and washed with water to remove salts from the filter cake. The filter cake is then dried, preferably by conventional spray drying to produce a precipitated silica containing about 3 to 10% moisture. If necessary, the precipitated silica may be milled to desired particle size by adjusting milling conditions. Because of the uniqueness of the process, milling conditions are easily adjusted to produce silica particles of desired mean values.

Preferred precipitated silica materials include those available from the J. M. Huber Corporation tinder the tradename, "Zeodent", particularly the silica carrying the designation "Zeodent 128" and "Zeodent CH 687-110-5".

The abrasive in the compositions described herein is present at a level of from about 6% to about 70%, preferably from about 15% to about 35% when the dentifrice is a toothpaste. Higher levels, as high as 95%, may be used if the composition is a toothpowder.

In addition to the above described essential components, the embodiments of this invention can contain a variety of optional dentifrice ingredients some of which are described below Optional ingredients include, for example, but are not limited to, adhesives, sudsing agents, flavoring agents, sweetening agents, additional anti-plaque agents, abrasives, and coloring agents. These and other optional components are further described in U.S. Pat. No. 5,004,597, Apr. 2, 1991 to Majeti; U.S. Pat. No. 4,885,155, Dec. 5, 1989 to Parran, Jr. et al.; U.S. Pat. No. 3,959,458, May 25, 1976 to Agricola et al. and U.S. Pat. No. 3,937,807, Feb. 10, 1976 to Haefele, all being incorporated herein by reference.

PHARMACEUTICALLY ACCEPTABLE CARRIER

The carrier for the components of the present compositions can be any dentifrice vehicle suitable for use in the oral cavity. Such carriers include the usual components of toothpastes, tooth powders, prophylaxis pastes, lozenges, gums and the like and are more fully described hereinafter. Toothpastes are the preferred systems.

Surfactants:

One of the preferred optional agents of the present invention is a surfactant, preferably one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

This surfactant can be present in the compositions of the present invention from about 0.1% to about 2.5%, preferably from about 0.3% to about 2.5% and most preferably from about 0.5% to about 2.0% by weight of the total composition.

Other suitable compatible surfactants can optionally be used along with the sarcosinate surfactant in the compositions of the present invention. Suitable optional surfactants are described more fully in U.S. Pat. No. 3,959,458, May 25, 1976 to Agricola et al.; U.S. Pat. No. 3,937,807, Feb. 10, 1976 to Haefele; and U.S. Pat. No. 4,051,234, Sep. 27, 1988 to Gieske et al. These patents are incorporated herein by reference.

Preferred anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be utilized.

Preferred cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., herein incorporated by reference, where said quaternary ammonium fluorides have detergent properties. Certain cationic surfactants can also act as germicides in the compositions disclosed herein. Cationic surfactants such as chlorhexadine, although suitable for use in the current invention, are not preferred due to their capacity to stain the oral cavity's hard tissues. Persons skilled in the art are aware of this possibility and should incorporate cationic surfactants only with this limitation in mind.

Preferred nonionic surfactants that can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Preferred betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramido propyl betaine.

Chelating agents:

Another preferred optional agent is a chelating agent selected from the group consisting of tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges which help hold this biomass intact. However, it is possible to use a chelating agent which has an affinity for calcium that is too high. This results in tooth demineralization and is contrary to the objects and intentions of the present invention.

Sodium and potassium citrate are the preferred alkali metal citrates, with sodium citrate being the most preferred. Also preferred is a citric acid/alkali metal citrate combination. Preferred herein are alkali metal salts of tartaric acid. Most preferred for use herein are disodium tartrate, dipotassium tartrate, sodium potassium tartrate, sodium hydrogen tartrate and potassium hydrogen tartrate. The amounts of chelating agent suitable for use in the present invention are about 0.1% to about 2.5%, preferably from about 0.5% to about 2.5% and more preferably from about 1.0% to about 2.5%. The tartaric acid salt chelating agent can be used alone or in combination with other optional chelating agents.

Other optional chelating agents can be used. Preferably these chelating agents have a calcium binding constant of about $10^1$ to $10^5$ provide improved cleaning with reduced plaque and calculus formation.

Another group of agents suitable for use as chelating agents in the present invention are the soluble pyrophosphates. The pyrophosphate salts used in the present compositions can be any of the alkali metal pyrophosphate salts. Specific salts include tetra alkali metal pyrophosphate, dialkali metal diacid pyrophosphate, trialkali metal monoacid pyrophosphate and mixtures thereof, wherein the alkali metals are preferably sodium or potassium. The salts are useful in both their hydrated and unhydrated forms. An effective amount of pyrophosphate salt useful in the present composition is generally enough to provide at least 1.0% pyrophosphate ion, preferably from about 1.5% to about 6%, more preferably from about 3.5% to about 6% of such ions. It is to be appreciated that the level of pyrophosphate ions is that capable of being provided to the composition (i.e., the theoretical amount at an appropriate pH) and that pyrophosphate forms other than $P_2O_7$–4 (e.g., ($HP_2O_7$–3)) may be present when a final product pH is established.

The pyrophosphate salts are described in more detail in Kirk & Othmer, *Encyclopedia of Chemical Technology*, Second Edition, Volume 15, Interscience Publishers (1968), incorporated herein by reference.

Still another possible group of chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Other operative polymeric polycarboxylates include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. both patents are incorporated herein by reference, and include copolymers of maleic anhydride with styrene, isobutylene or ethyl vinyl ether, polyacrylic, polyitaconic and polymaleic acids, and sulfoacrylic oligomers of M.W. as low as 1,000 available as Uniroyal ND-2.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al, in U.S. Pat. No. 4,051,234, Sep. 27, 1977, incorporated herein by reference.

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al., both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gun, gum arabic, and gum tragacanth can also be used. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Also desirable for inclusion in the compositions of the present invention are other stannous salts such as stannous pyrophosphate and stannous gluconate and antimicrobials such as quaternary ammonium salts, such as cetyl pyridinium chloride and tetradecylethyl pyridinium chloride, bis-biquanide salts, copper bisglycinate, nonionic anti microbial salts and flavor oils. Such agents are disclosed in U.S. Pat. No. 2,946,725, Jul. 26, 1960, to Norris et al. and U.S. Pat. No. 4,051,234, Sep. 27, 1977 to Gieske et al., incorporated herein by reference. Other optional components include buffering agents, bicarbonates, peroxides, nitrate salts such as sodium and potassium nitrate. These agents, if present, are included at levels of from about 0.01% to about 30%.

Other useful carriers include biphasic dentifrice formulations such as those disclosed in U.S. Pat. Nos. 5,213,790, issued May 23, 1993, 5,145,666, issued Sep. 8, 1992, and 5,281,410 issued Jan. 25, 1994 all to Lukacovic et al. and in U.S. Pat. Nos. 4,849,213 and 4,528,180 to Schaeffer the disclosures of which are incorporated by reference herein.

Suitable lozenge and chewing gum components are disclosed in U.S. Pat. No. 4,083,955, Apr. 11, 1978 to Grabenstetter et al., incorporated herein by reference.

The following examples further describe and demonstrate preferred embodiments within the scope of the present invention. The examples are given solely for illustration and are not to be construed as limitations of this invention as many variations are possible without departing from the spirit and scope thereof.

EXAMPLE I

A dentifrice composition of the present invention contains the following components as described below.

| Component | Wgt % |
| --- | --- |
| Sorbitol 70% soln | 24.200 |
| RO Water | 24.757 |

11 -continued

| Component | Wgt % |
| --- | --- |
| Glycerin | 7.000 |
| Carboxymethyl Cellulose[1] | 0.500 |
| PEG 6 | 4.000 |
| Sodium Fluoride | 0.243 |
| Sodium Saccharine | 0.130 |
| Monosodium Phosphate | 0.415 |
| Trisodium Phosphate | 0.395 |
| Sodium Tartrate | 1.000 |
| TiO2 | 0.500 |
| Silica[2] | 35.000 |
| Sodium Lauroyl Sarcosinate (95% active) | 1.060 |
| Flavor | 0.800 |

[1]Supplied by Aqualon Company.
[2]Available as Zeodent 128 from J. M. Huber Corporation and possesses the following characteristics: APS Mean Value = 13.4 microns, oil absorption = 95 cc/100 g, HGI Void Volume = 1.95 cc/g, PCR = 117, RDA = 79.

The jacket temperature of a mixing tank is set to about 150° F. (65° C.) to about 160° F. (71° C.). The humectants and water are added to the mixing tank and agitation is started. When the temperature reaches approximately 120° F. (50° C.) fluoride, sweetening agents, buffering agents, chelant, coloring agents and titanium dioxide are added. Thickening agents are added to the abrasive and the resulting mixture is added to the mixing tank with high agitation. The surfactant is added to the combination and mixing is continued. The tank is cooled to 120° F. (50° C.) and the flavoring agents are added. Mixing is continued for approximately 5 minutes. The resulting composition will have a pH of about 7.

EXAMPLE II

A dentifrice composition of the present invention contains the following components as described below.

| Component | Wgt % |
| --- | --- |
| Sorbitol 70% soln | 29.810 |
| RO Water | 24.757 |
| Glycerin | 7.000 |
| Carboxymethyl Cellulose[1] | 0.750 |
| PEG 6 | 4.000 |
| Sodium Fluoride | 0.243 |
| Sodium Saccharine | 0.130 |
| Monosodium Phosphate | 0.415 |
| Trisodium Phosphate | 0.395 |
| TiO2 | 0.500 |
| Silica[2] | 30.000 |
| Sodium Lauryl Sulfate | 1.200 |
| Flavor | 0.800 |

[1]Supplied by Aqualon Company.
[2]Available as Zeodent 128 from J. M. Huber Corporation and possesses the following characteristics: APS Mean Value = 13.4 microns, oil absorption = 95 cc/100 g, HGI Void Volume = 1.95 cc/g, PCR = 117, RDA = 79.

EXAMPLE III

A gum composition of the present invention contains the following components as described below.

| Component | Weight % |
| --- | --- |
| Gum Base | 30.000 |
| 30 parts Estergum | |
| 45 parts Coumorone Resin | |
| 15 parts Dry Latex | |
| Silica[1] | 10.00 |

| Component | Weight % |
| --- | --- |
| Sugar | 40.000 |
| Corn Syrup | 18.175 |
| Sodium Lauroyl Sarcosinate | 0.075 |
| Sodium Tartrate | 0.250 |
| Flavor | 1.500 |

[1]This silica possesses the following characteristics: APS Mean Value = 10.8 microns, oil absorption = 90 cc/100 g, HGI Void Volume = 1.7 cc/g, PCR = 109, RDA = 87.

What is claimed is:

1. A dentifrice composition comprising:
   a. a precipitated silica, said precipitated silica being a low structure precipitated silica having a narrow particle size range distribution of soft particles and having a mean value (MV) particle size ranging from 8 to 14 microns, an oil absorption ranging from 60 to 120 cc/100 g, and a mercury intrusion (HGI) void volume of 1.0 to 4.0 cc/g; said precipitated silica, when formulated into a-dentifrice, having a Pellicle Cleaning Ratio (PCR) of from 70 140 and a Radioactive Dentin Abrasion (RDA) value of from 60 to 130; and wherein the ratio of said PCR to said RDA is at least 1.1; and wherein, as the particle size in microns increases in said silica, the RDA value remains substantially constant; and
   b. from about 0.1% to about 99% of an orally-acceptable dentifrice carrier.

2. A dentifrice composition according to claim 1 wherein said abrasive has an RDA, when formulated into a dentifrice formulation, ranging from 60 to 98, a BET surface area ranging from 50 to 250 m$^2$/g, a pH of 5 percent water slurry ranging from 4.0 to 8.5 wherein said silica particles are of substantially uniform particle size with a very narrow distribution within the MV particle size of from 8 to 14 microns, and wherein smaller particles are cohesively adhered to each other by physical binding to be within said MV particle size.

3. A dentifrice composition according to claim 2, wherein the median average particle size of said particles ranges from about 7 to 11 microns.

4. A dentifrice composition according to claim 3 wherein said composition further comprising a fluoride ion source wherein the fluoride ion source is selected from the group consisting of sodium fluoride, stannous fluoride, sodium monofluorophosphate, potassium fluoride and mixtures thereof.

5. A dentifrice composition according to claim 4 which further comprises a surfactant selected from the group consisting of sarcosinate surfactants, isethionate surfactants and taurate surfactants.

6. A dentifrice composition according to claim 5 which further comprises from about 0.1% to about 2.5% of a chelating agent selected from the group consisting of tartaric acid and pharmaceutically-acceptable salts thereof, citric acid and alkali metal citrates and mixtures thereof.

7. A dentifrice composition according to claim 6 wherein said composition has a pH above about 7 and wherein the surfactant is selected from the group consisting of sodium lauroyl sarcosinate, sodium decyl sarcosinate, sodium myristyl sarcosinate, sodium stearyl sarcosinate, sodium palmitoyl sarcosinate, sodium oleoyl sarcosinate and mixtures thereof.

8. A dentifrice composition according to claim 7 further comprising from about 15% to about 70% of a humectant selected from among the group consisting of glycerin, sorbitol, Propylene glycol and mixtures thereof.

9. A dentifrice composition according to claim 8 wherein the surfactant is a combination of sodium lauroyl sarcosinate and cocoamidopropyl betaine and the chelating agent is a combination of tartaric acid and sodium tartrate.

10. A dentifrice composition according to claim 1 in the form of a toothpaste, tooth powder, prophylaxis paste, lozenge, gum, or oral gel.

11. A dentifrice composition comprising the steps of:
 a. a precipitated silica, wherein said silica is prepared by the following steps:
  i) providing an aqueous solution of sodium silicate having a concentration of about 8.0 to 35 weight percent, and an $Na_2O:SiO_2$ ratio of about 1 to 3.5:1;
  ii) providing a sulfuric acid aqueous solution having a concentration of about 6 to 35 percent;
  iii) charging to a reactor about 1 to 5 percent of the stoichiometric amount of said sodium silicate solution with agitation;
  iv) heating said solution of said sodium silicate to a temperature in the range of about 80° to 90° C.;
  v) slowly adding to said reactor, sulfuric acid and the remainder of said sodium silicate solution, said addition being conducted over a period of time wherein the sodium silicate is metered into the reaction mixture at the rate of about 7 to 12 liters per minute and the sulfuric acid is metered into the reactor at the rate of about 1 to 4 liters per minute;
  vi) continuing the addition of sodium silicate and sulfuric acid to said reactor over an addition time of about 40 to 60 minutes;
  vii) stopping the sodium silicate solution addition but continuing the sulfuric acid solution addition with agitation until a final pH of 5.0 to 5.8 is obtained in the reactor to provide a precipitated silica in the reaction liquor;
  viii) raising the temperature of said reaction mixture to a temperature of about 90° to 98° C. for a time of about 10 minutes to 1 hour while continuing agitation; and
  ix) curing the reaction mixture by boiling said mixture for a period of at least about 30 minutes to two hours to cause formation of substantially uniform particle size precipitated silica;
  x) cooling the reaction mixture and recovering the precipitated silica; and
 b. from about 0.1% to about 99% of an orally-acceptable dentifrice carrier.

12. A dentifrice composition according to claim 1 wherein greater than about 2% of said precipitated silica are agglomerated.

13. A dentifrice composition according to claim 12 wherein greater than about 5% of said precipitated silica are agglomerated.

14. A dentifrice composition according to claim 4 wherein greater than about 5% of said precipitated silica are agglomerated.

15. A method for reducing stain and/or plaque and gingivitis comprising the application of a safe and effective amount of a composition according to claim 1, to the teeth and other oral surfaces.

16. A method for reducing stain and/or plaque and gingivitis comprising the application of a safe and effective amount of a composition according to claim 4, to the teeth and other oral surfaces.

17. A method for reducing stain and/or plaque and gingivitis comprising the application of a safe and effective amount of a composition according to claim 7, to the teeth and other oral surfaces.

18. A method for reducing stain and/or plaque and gingivitis comprising the application of a safe and effective amount of a composition according to claim 11, to the teeth and other oral surfaces.

* * * * *

UNITED STATES PATENT AND TRADEMARK OFFICE
CERTIFICATE OF CORRECTION

PATENT NO. : 5,603,920

DATED : February 18, 1997

INVENTOR(S) : David E. Rice

It is certified that error appears in the above-identified patent and that said Letters Patent is hereby corrected as shown below:

Column 2, line 64 "(RE)A)" should read --RDA--.

Column 3, line 29, "sorer" should read --softer--

Column 6, line 54 "below" should read --below. --

Signed and Sealed this

Twenty-fourth Day of February, 1998

Attest:

BRUCE LEHMAN

*Attesting Officer*     Commissioner of Patents and Trademarks